(12) United States Patent
Lagae et al.

(10) Patent No.: US 7,719,280 B2
(45) Date of Patent: May 18, 2010

(54) DETECTION OF RESONANT TAGS BY ULTRA-WIDEBAND (UWB) RADAR

(75) Inventors: Liesbet Lagae, Herent (BE); Gustaaf Borghs, Leuven (BE)

(73) Assignee: IMEC, Leuven (BE)

( * ) Notice: Subject to any disclaimer, the term of this patent is extended or adjusted under 35 U.S.C. 154(b) by 192 days.

(21) Appl. No.: 11/750,155

(22) Filed: May 17, 2007

(65) Prior Publication Data

US 2008/0252293 A1    Oct. 16, 2008

Related U.S. Application Data

(60) Provisional application No. 60/802,578, filed on May 22, 2006.

(30) Foreign Application Priority Data

May 23, 2006    (EP)    .................................. 06447069

(51) Int. Cl.
*G01V 3/00* (2006.01)
(52) U.S. Cl. ...................................... 324/322; 324/318
(58) Field of Classification Search ......... 324/300–322; 600/407–445; 378/4, 15, 901; 455/456.1, 455/456.2, 133; 342/450
See application file for complete search history.

(56) References Cited

U.S. PATENT DOCUMENTS

| 4,940,966 | A | | 7/1990 | Pettigrew et al. |
| 4,979,186 | A | | 12/1990 | Fullerton |
| 5,361,070 | A | | 11/1994 | McEwan |
| 5,510,800 | A | | 4/1996 | McEwan |
| 5,661,490 | A | | 8/1997 | McEwan |
| 5,668,555 | A | * | 9/1997 | Starr .......................... 342/179 |

(Continued)

FOREIGN PATENT DOCUMENTS

WO    WO 2003/042919 A2    5/2003

(Continued)

OTHER PUBLICATIONS

Aydin, et al.; Investigation of magnetic resonances for different split-ring resonator parameters and designs; New Journal of Physics 7 (2005) 168.

(Continued)

*Primary Examiner*—Brij B Shrivastav
(74) *Attorney, Agent, or Firm*—Knobbe Martens Olson & Bear LLP

(57) ABSTRACT

A detection system having a receiver for detecting a material having a magnetic resonance response to illumination by pulses of ultra-wideband (UWB) electromagnetic radiation is disclosed. The receiver comprises a detector for detecting the pulses after they have interacted with the material, and a discriminator arranged to identify in the detected pulses the magnetic resonance response of the material. By scanning an item tagged with a tag having a material having a magnetic resonant response, by illuminating the item with UWB pulses and identifying in detected pulses the magnetic resonance response of the material, items can be located, imaged, or activated. The magnetic resonance response of the tag can cause activation of the tag. The tag can have a magnetic resonance response arranged to provide an identifiable magnetic resonance signature such that different tags can be identified and distinguished by their signatures.

32 Claims, 8 Drawing Sheets

U.S. PATENT DOCUMENTS

| | | | |
|---|---|---|---|
| 5,766,208 | A | 6/1998 | McEwan |
| 6,771,732 | B2* | 8/2004 | Xiao et al. .................. 378/4 |
| 6,914,552 | B1 | 7/2005 | McEwan |
| 6,924,150 | B1 | 8/2005 | Xiang et al. |
| 7,260,369 | B2* | 8/2007 | Feher .................. 455/133 |
| 7,273,580 | B2* | 9/2007 | Kirsten et al. ........... 264/489 |
| 7,356,343 | B2* | 4/2008 | Feher .................. 455/456.1 |
| 2004/0026028 | A1 | 2/2004 | Kirsten et al. |
| 2004/1100376 | | 5/2004 | Lye, et al. |
| 2004/0138554 | A1 | 7/2004 | Dimmer et al. |
| 2004/0249257 | A1* | 12/2004 | Tupin et al. ............. 600/407 |
| 2005/0096589 | A1 | 5/2005 | Shachar |
| 2005/0179552 | A1 | 8/2005 | Shoji et al. |

FOREIGN PATENT DOCUMENTS

WO    WO 2004/107954 A2    12/2004

OTHER PUBLICATIONS

Converse, et al.; A Computational Study of Ultra-Wideband Versus Narrowband Microwave Hyperthermia for Breast Cancer Treatment; IEEE Transactions on Microwave Theory and Techniques (Online); IEEE 2006; XP-002397315.

Robert Fontana; Recent System Applications of Short-Pulse Ultra-Wideband (UWB) Technology; IEEE Transactions on Microwave Theory and Techniques (Online), vol. 52, No. 9; Sep. 2004; XP-002397316.

Moreland, et al.; Ferromagnetic resonance spectroscopy with a micromechanical calorimeter sensor; Review of Science Instruments, vol. 71, No. 8; Aug. 2000.

Nicholson, et al.; Applications of Time-Domain Metrology to the Automation of Broad-Band Microwave Measurements; IEEE Transactions on Microwave Theory and Techniques, vol. MTT-20, No. 1; Jan. 1972.

Tan, et al.; UWB Radar Transceiver and Measurement for Medical Imaging; 2004 IEEE International Workshop on Biomedical Circuits & Systems; Piscataway, NJ; December 204; XP010809986.

http://www.aetherwire.com/CDROM/General/numbers.htm; Patents Related to Ultra-Wideband Technology; printed from Internet on Feb. 12, 2008.

Enrico M. Staderini; UWB Radars in Medicine; IEEE AESS Systems Magazine, Jan. 2002.

International Search Report for PCT/BE2007/000049 dated Aug. 27, 2007.

Written Opinion of the International Searching Authority for PCT/BE2007/000049 dated Aug. 27, 2007.

European Search Report for EP 06447069.3 dated Oct. 4, 2006.

Official Communication dated Apr. 21, 2009, issued in European Patent Application No. 07719213.6.

* cited by examiner

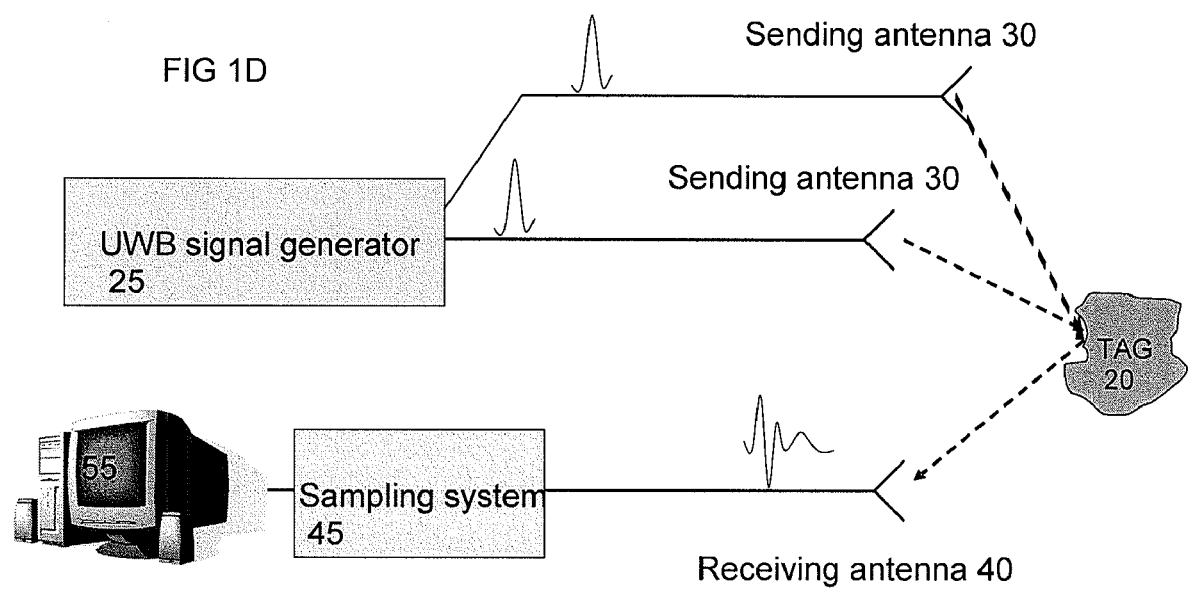

FIG 2A:
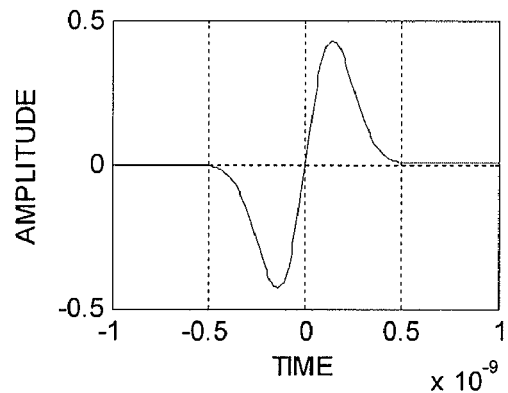
FIG 2B
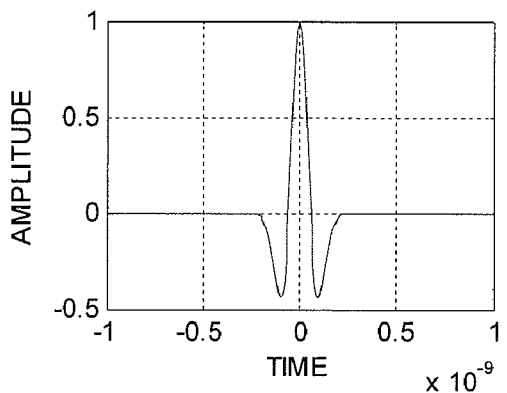
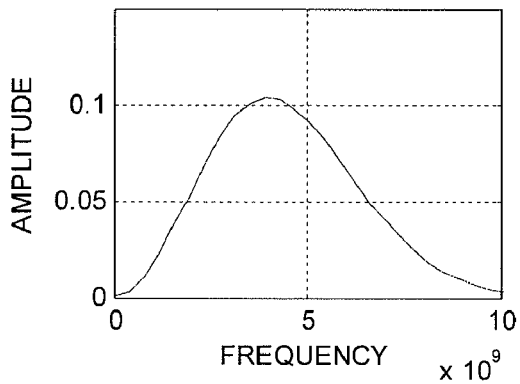
FIG 2C
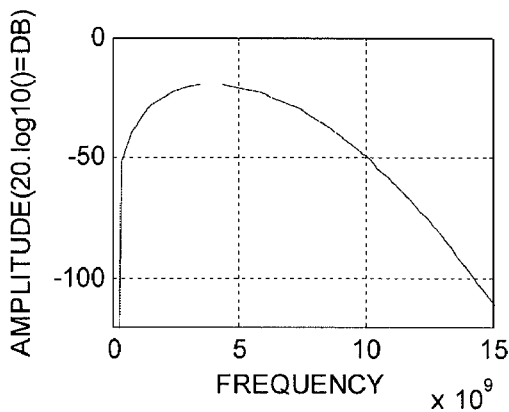
FIG 2D
Fig. 3A:
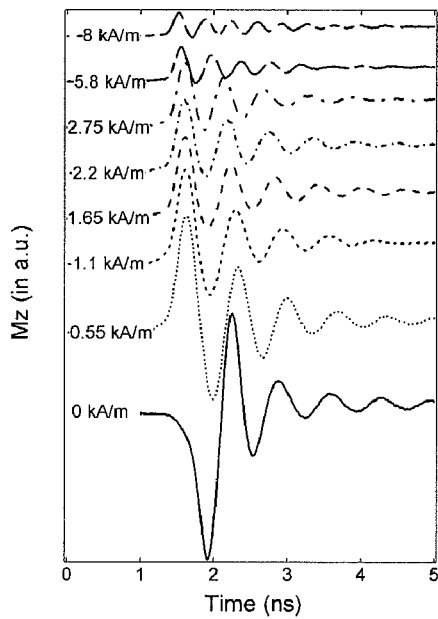
Fig 3B:
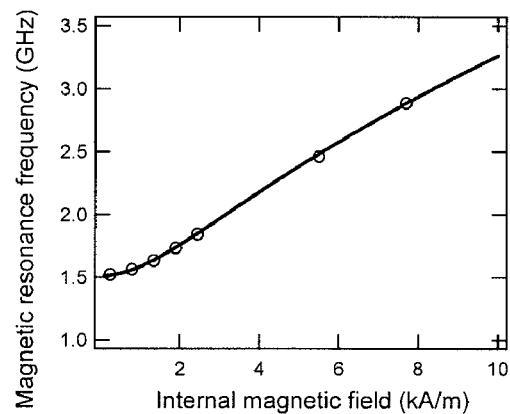

DETECTION OF RESONANT TAGS BY ULTRA-WIDEBAND (UWB) RADAR

CROSS REFERENCE TO RELATED APPLICATIONS

This application claims priority under 35 U.S.C. §119(e) to U.S. provisional patent application 60/802,578 filed on May 22, 2006, which application is hereby incorporated by reference in its entirety.

BACKGROUND OF THE INVENTION

1. Field of the Invention

This invention relates to detection systems using ultra-wideband (UWB) pulses to detect magnetic resonance responses, to receivers for such systems, and to corresponding methods and software for carrying out the methods, and to methods of using UWB pulses to activate tags having a magnetic resonance response and to tags for such apparatus and methods.

2. Description of the Related Technology

Radar is well known and is based on the property that metallic objects cause strong reflection of electromagnetic radiation in air due to strong impedance contrast. Metallic objects have a complex wave impedance, approximately equal to $Z=(1+j)/\sigma\delta$ with $\delta$ the characteristic depth of penetration of the waves, also called the skin depth. The waves will penetrate at the metal surface over a couple of skin depths and some absorption may occur in that surface layer. Most of the power will reflect at the metal surface. U.S. Pat. No. 5,766,208 mentions that if a metallic object such as a pace maker is present in the body, then the reflected signal will be dominated by the pace maker reflection, since the reflection coefficient approaches 1.0 for the metal object. US2005/0096589 mentions the use of an ultra-wideband or impulse radar (UWB) in order to probe the position of a catheter with magnetic tip, from which the backscattered electromagnetic radiation is measured while guiding its position using magnetic gradient forces. Only the reflection, caused by the contrast between the dielectric properties of the normal tissue and the catheter tip is used to detect the tip in this case (similar to metallic tags). Moreover, the magnetic fields used for the guidance of the catheter change the magnetic resonance continuously, thereby complicating the use of the resonant feature as a unique signature.

The use of magnetic medium to act as identification tags is already applied in magnetic RF-ID tags that consist of a magnetic medium which is detected when the article to which it is attached passes through a detection system, which emits an alternating narrow-band magnetic interrogation field of 50 Hz-100 KHz. Several patents (e.g. U.S. Pat. No. 4,940,966) discuss inventive magnetic bar coding or tagging principles based on distinctive physical parameters (e.g. shape, magnetic material, distance and orientation with respect to another tag). UWB radar technology is known for positioning of large articles (e.g. car identification, through wall vision) and motion sensing. An overview on the patents created on UWB is available at: http://www.aetherwire.com/CDROM/General/Numbers.html Some of the most relevant patents here are: Time-of-Flight Radio Location System [U.S. Pat. No. 5,661,490 and U.S. Pat. No. 5,510,800], Time Domain Radio Transmission-System [U.S. Pat. No. 4,979,186] and UWB radar motion sensor [U.S. Pat. No. 5,361,070]

Also known are pulsed magnetrons at GHz frequencies, used for heating molecules (i.e. food). These are narrow-band and no tags are involved.

Use of UWB technology is known in medicine as follows: radar technology, [e.g. fetal heart and breath rate and uterine contractions as shown in http://www.uniroma2.it/fismed/UWBradar/MedicalUWB.html, U.S. Pat. No. 5,766,208 and WO2004107954]

UWB signal communications to send/receive (implanted) biosensor readings as time domain pulse trains E.g. US2004100376. Such a biosensor can indicate biochemical (infections, hormones) but also physical (e.g. monitoring uterine contractions using electrodes on the body etc.) events.

Also known is Magnetoradar: Detection of mechanically excited object at a harmonic frequency of a varying magnetic field utilizing UWB radar motion sensors, as shown in U.S. Pat. No. 6,914,552.

Ferro- and ferri-magnetic nanoparticles are known for use as contrast agent in MR (Magnetic Resonance) imaging applications (at low frequencies) and for FMR imaging [U.S. Pat. No. 6,924,150].

UWB is known for scanning and imaging applications [WO03042919].

Magnetic RF-ID tags are known in U.S. Pat. No. 4,940,966 and implantable resonator circuits (LC tanks) including magnetic material in the inductor are shown in US2004138554 and US2005179552.

Magnetothermia (heating/destroying of cells) by specific uptake of nanoparticles and selective heating using AC magnetic fields below approx. 1 MHz is known. Heating of substrates by electromagnetic radiation at ferromagnetic resonance frequencies (1-300 GHz) is shown in US2004026028 and in [John Moreland, et al., Rev. of Sci. Instr., Vol 71 p 3088].

Current UWB systems have limited spatial accuracy in free space, in the human body with high refraction indices at UWB frequencies, sub mm position accuracy is possible if the signal losses are not too high. Current UWB systems have low signal-to-noise and signal-to-clutter ratio (for given maximal value of the Specific Absorption Rate (SAR-value) given by official regulations) due to high losses at high frequency in the body and multipath reflections.

SUMMARY OF CERTAIN INVENTIVE ASPECTS

An object of certain inventive aspects is to provide improved apparatus or methods for detection using UWB, to provide receivers for such systems, and/or corresponding methods and software for carrying out the methods, and/or methods of using UWB pulses to activate tags and/or tags for such apparatus and methods. A first inventive aspect relates to a detection system comprising a transmitter for transmitting a series of pulses of UWB electromagnetic radiation, at least one receiver for identifying echo pulses of the series of pulses and being adapted to identify a signature imposed on the echo pulses, the signature being indicative of material exhibiting magnetic resonance induced by the series of pulses.

Another aspect is a receiver for receiving echoes of a series of pulses of UWB electromagnetic radiation, and comprising:
means to identify a signature imposed on the echo pulses, the signature being indicative of reflection from a material exhibiting magnetic resonance induced by the series of pulses.

Another aspect is the receiver having a correlator circuit for identifying echo pulses from the series of pulses and also for identifying the signature.

Another aspect is a receiver for detecting a material having a magnetic resonance response to illumination by pulses of UWB electromagnetic radiation, the receiver having: a detector for detecting the pulses after they have interacted with the material, and a discriminator arranged to identify in the detected pulses the magnetic resonance response of the material.

Another aspect provides a method of scanning an item tagged with a tag having a material having a magnetic resonant response, the method having the steps of illuminating the item with pulses of UWB electromagnetic radiation, detecting the pulses after they have interacted with the material, and identifying in the detected pulses the magnetic resonance response of the material.

Another aspect provides a method of activating a tag in an item, the tag having a material having a magnetic resonant response, the method having the step of illuminating the item with pulses of UWB electromagnetic radiation, such that the magnetic resonance response of the tag causes activation of the tag.

Another aspect provides a tag for use by the system, receiver or method, the tag having a material having a magnetic resonance response arranged to provide an identifiable magnetic resonance signature response to illumination by pulses of UWB radiation, such that different tags can be identified and distinguished by their signatures.

Any of the additional features can be combined together and combined with any of the aspects. Other advantages will be apparent to those skilled in the art, especially over other prior art. Numerous variations and modifications can be made without departing from the scope of the present invention. Therefore, it should be clearly understood that the form of the present invention is illustrative only and is not intended to limit the scope of the present invention.

Another aspect relates to a method of scanning an item tagged with a tag having a material having a magnetic resonant response. The method comprises illuminating the item with pulses of UWB electromagnetic radiation. The method further comprises detecting the pulses after they have interacted with the material. The method further comprises identifying in the detected pulses the magnetic resonance response of the material.

Another aspect relates to a method of activating a tag in an item, the tag having a material having a magnetic resonant response. The method comprises illuminating the item with pulses of UWB electromagnetic radiation, such that the magnetic resonance response of the tag causes activation of the tag.

BRIEF DESCRIPTION OF THE DRAWINGS

Certain inventive aspects will now be described by way of example with reference to the appended drawings, in which:

FIGS. 1A, 1B, 1C, 1D and 1E show overall views of examples of systems using UWB radar to detect magnetic resonant features of a tag, with separate receive and transmit antennas or with a single antenna, or multiple receive or transmit antennas, or receive antenna located for detecting transmissions through the tag, according to embodiments of the invention.

FIGS. 2A, 2B, 2C and 2D show graphs of typical UWB signals in the time domain and frequency domain, a gaussian monocycle for transmission is shown in FIG. 2A, a gaussian doublet is the derivative of a monocycle, the result of transmission of a monocycle by a dipole antenna, is shown in FIG. 2B, a frequency spectrum of this signal is shown in FIG. 2C, and in a logarithmic (dB) scale in FIG. 2D.

FIG. 3A shows a graph of an experimentally determined time domain response of a ferromagnetic tag when impinged by a step pulse, showing different waveforms for different values of an externally applied DC magnetic bias field.

FIG. 3B shows a graph showing dependence of the resonant frequency on the internal magnetic field, consisting of the external DC bias field, the internal anisotropy field and the applied step pulse.

FIG. 7A shows examples of different shapes of ferromagnetic tags. FIG. 7B shows pictures of medium loaded with ferromagnetic tags. FIG. 7C shows different shapes of metallic particles, that show a magnetic resonance due to their specific designed geometry. FIG. 7D shows a metamaterial consisting of an array of metal particles.

DESCRIPTION OF CERTAIN INVENTIVE EMBODIMENTS

Figure 1A:
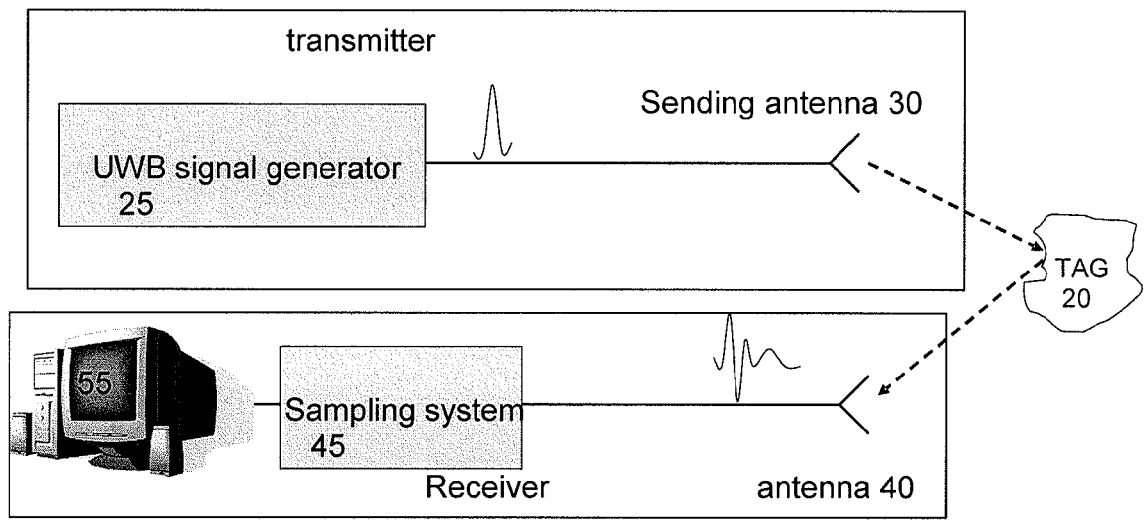

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present description, the only relevant components of the device are A and B.

Embodiments of this invention relate to the application of Ultrawide band (UWB) radar technology for detecting a response from magnetic resonant tags. This has a wide range of applications, notably including medical monitoring/positioning/imaging device for health applications. UWB radar technology allows probing internal parts of the human body by time domain reflectometry with submillimeter resolution due to the high refraction index of human tissue. Due to the high attenuation losses in the human body, the signal-to-noise is typically very low even for high pulse powers. By using tags that have a magnetic resonant feature for electromagnetic radiation in a frequency range compatible with the UWB frequency range a ferromagnetic resonance signature appears on the received UWB radio signal. The identification of that signature in the receiver e.g. by time correlations can drastically enhance the signal-to-noise and signal-to-clutter of UWB reflected/transmitted signal by an object. The resonant excitation of the tag by UWB radiation can also be used to induce biochemical reactions in the body.

The magnetic resonant features have never been used in an RF-ID identification procedure before since the frequencies necessary to probe the magnetic resonance (>500 MHz) have never been used for RF-ID's since these higher frequencies are attenuated more than lower frequencies by objects in the path, e.g. by the article to identify.

Ultra Wide Band Radars

Ultra wide band systems are short range wireless communication and/or radar systems. that exploit the fact that ultra-short duration pulses with ultra-wide bandwidths have excellent immunity to fading and interferences from other narrow-band sources. Ultra wideband radar is defined as any radar whose fractional bandwidth is greater than about 0.2, regardless of the center frequency or the signal time-bandwidth product. UWB radar technology focuses on the pulse responses upon reflection/transmission of UWB signals in time by an object thereby giving accurate information on the object's position, shape, etc. The pulses are typically shorter than a nanosecond in time duration. This translates to a frequency domain signal with center frequencies typically between about 500 MHz and 20 GHz; and ultra-wide bandwidths of minimal 20% or 25% and up to 200% of the center frequency.

The strength of UWB relies on the time domain properties, rather than the conventionally used frequency domain. When a receiver only "listens" when the transmitted pulse is expected to arrive, a high noise rejection and multipath or clutter immunity can result. Because the UWB pulse is spread across an extremely wide frequency range and is limited in time, the power sampled at a single, or specific frequency is very low. In 1994, T. E. McEwan, invented the Micropower Impulse Radar (MIR), where the read-out is based on gating of the receiver based on time-of-arrival of the pulse response coming from the target at the location of the receiving antenna. The spatial resolution is determined by the 'spatial length', which is the pulse duration times the speed of light in the medium. An effective method of detection is to sample and analyze the received signal e.g. by calculating time correlations between different reflected signals, where the correlations are made using a high temporal resolution (<approximately 200 ps). Detection of the position of a target can thus be performed by threshold detection (in the case of a gating receiver) or maximal correlation detection.

Time correlation of two functions $y1(t)$ and $y2(t)$ are mathematically described by the cross-correlation function $z(t)$. An equivalent frequency domain description is given by the corresponding frequency domain correlation function $Z(f)$.

$$z(t) = \int_{-\infty}^{+\infty} y_1(t)^* \cdot y_2(t+\tau) \, d\tau = y_1(t)^* y_2(t)$$

or $$Z(f) = Y1(f)^* \cdot Y2(f)$$

where * denotes the complex conjugate function and where $\tau$ is the time lag. Note that the correlation in the frequency domain is a multiplication of the complex conjugate of the frequency domain input function $Y1(f)$ and the input function $Y2(f)$ to produce the correlation function $Z(f)$.

Auto-correlation correlates a signal with a preserved copy of the same signal at another time $$z(t) = \int_{-\infty}^{+\infty} y(\tau)^* \cdot y(t+\tau) \cdot d\tau = y(t)^* y(t)$$

or $$Z(f) = |Y1(f)|^2.$$

In the case of UWB signals auto-correlations and cross-correlations are used to extract information from received signals. I.e. when a received signal $y_1(t) = a \cdot x_1(t+t_1)$ reflected from a perfect reflecting target is correlated with a stored version of the transmitted signal $x_1(t)$, we get $$z(t) = \int_{-\infty}^{+\infty} ax_1(\tau + t_1)^* x_1(t + \tau) \, d\tau$$

with $t_1$ the time-of-flight of the signal from transmitter to receiver. Notice that the autocorrelation function $z(t)$ is maximum when the time $t$ equals the time-of-flight. It is obvious that time correlations offer the possibility to accurately calculate distances from the target to a transceiver, or between different targets, transmitters and receivers. More complex correlation processing of signals transmitted by multiple antennas at the transmitter/receiver side can yield precise estimations of the angle-of-arrival, the absolute or relative position, of the object or different objects. For example, when a linear array of antennas is used, the signal received by the i-th element of the array has a time delay with respect to the (i−1)-th antenna and the delay is a function of the direction of arrival and the geometry of the array. By correlating the signals received by multiple antennas the angle of incidence can be estimated. The error on this estimation will be reduced when more received signal waveforms are correlated. The spatial resolution of the radar is ultimately determined by the time resolution with which the correlations can be calculated, and that is typically the sampling rate of the receiver, i.e. 200 ps time resolution will correspond to a spatial resolution of 6 cm in air, and 2 ps time resolution will yield a spatial resolution of 0.6 mm in air. These time correlation methods have brought the state-of-the-art of UWB radar applications down to three-dimensional subcentimeter positioning and tracking at the expense of calculation times and high-performance receivers. UWB radar technology based on time correlations is already on the market for sub-centimeter target detection (e.g. Time Domain Inc. with a center frequency 4.7 GHz and an absolute bandwidth of 3.2 GHz (fractional bandwidth 68%)) and a pulse repetition frequency up to 9.6 MHz.

The characteristic behavior of a target object is typically described through its characteristic time domain impulse response function h(t) which transforms an input signal x(t) to an output signal y(t) by mathematical convolution.

$$y(t) = \int_{-\infty}^{+\infty} h(\tau).x(t-\tau).d\tau = h(t) \otimes x(t)$$

or $$Y(f) = H(f).X(f)$$

Note that the convolution in the frequency domain is a multiplication of the frequency domain input function X(f) and transfer function H(f) to produce the frequency domain output function Y(f). The transfer function h(t) or H(f) of the target will influence both the phase and amplitude of the radiation upon transmission or reflection. The received signal contains information about the frequency spectrum of the target, and can be used not only to do target positioning but also target identification, characterization and even imaging when the full time domain signal waveforms are received and analyzed. The time domain impulse response y(t) scattered from or transferred through a target when x(t) is a Dirac impulse function is equal to the scattering or transfer function h(t) and thus contains a characteristic signature of the target. When not only information on the location but also some information on the target itself is required, the signal waveform y(t) must be received and analyzed with sufficient bandwidth to preserve the modulations impressed on the signal by the target.

Microwave theory generally models targets by multi-port microwave networks using scattering (S)-parameters or impedance (Z)-parameters (both are equivalent descriptions) compatible with Maxwell's equations for electromagnetic waves. The S- or Z-parameters can be probed over a wide frequency band and contain the response of the target and depend in a complex way on the complex permittivity $\varepsilon$ and permeability $\mu$ of that target. The characteristic wave impedance of a medium is an expression of the relationship between the electric-field and magnetic-field intensities in an electromagnetic field and is in general given by $$Z = \sqrt{\frac{\mu}{\varepsilon}} \cdot \sqrt{\frac{1}{1-j\frac{\sigma}{\omega\varepsilon}}} \quad \text{reducing to} \quad [1]$$

$$Z^{dielectric} \approx \sqrt{\frac{\mu}{\varepsilon}} = \sqrt{\frac{\mu_r}{\varepsilon_r}} \sqrt{\frac{\mu_0}{\varepsilon_0}} = \sqrt{\frac{\mu_r}{\varepsilon_r}} Z_0$$

for a dielectric, where $Z_0$ is the characteristic wave impedance of free space (air), $\sigma$ the conductivity of the medium, $\omega$ the radial frequency and $\varepsilon$ and $\mu$ the permittivity and permeability respectively. When a wave is incident from free space on a target surface, continuity of Maxwell's equations predicts that the reflection coefficient will be given by $(Z_{target}-Z_0)/(Z_{target}+Z_0)$, and the transmission coefficient by $2.Z_{target}/(Z_{target}+Z_0)$. Similarly the time domain waveform of the scattered waves contains information about the complex permittivity $\varepsilon$ and permeability $\mu$ of the target (For more details, see 'Applications of Time domain Metrology to the Automation of Broad Band Microwave measurements' A. M. Nicholson et al. IEEE Trans. On Microwave Theory and techniques, vp; 20, no. 1 (1972), which is incorporated herein in its entirety by reference).

The main disadvantage of UWB radars/sensors is that the transmitted UWB pulse interacts with a variety of objects and can be scattered in a complex way before reaching the receiver. Radars working at lower frequencies only interact with large objects, but UWB radars interact with many smaller objects along the way, resulting in multipath reflections at the receiver. Clutter in a radar system is defined as unwanted signals having similar characteristics and appearing in the same time window as the target response. Therefore, clutter from objects of no interest will lower the sensitivity for target identification or detection. Most methods for enhancing the target's signal-to-noise and signal-to-clutter ratio consist of advanced signal processing, using time-frequency approaches and/or digital Finite Impulse Response (FIR) filtering. Most known UWB devices use UWB signals to send, receive and interpret target scatterings without employing any tags.

Magnetic Resonant Materials as Tags

Embodiments of this invention use magnetic resonant materials as a tags to label the target unambiguously, thereby increasing the signal-to-noise ratio for positioning and identification applications, especially in environments where the clutter is high, e.g. in the human body. Embodiments of the invention address the problems of low signal-to-noise and signal-to-clutter ratios by using magnetic resonant tags that identify the targets of interest by a very specific signature, e.g. a change in pulse shape, time lag, polarization, or frequency spectrum (amplitude and phase) of the pulse. Signal processing algorithms can be optimized towards the specific signature of the tags, to increase the signal-to-noise ratio and to get very accurate positioning information on the tag. For example, time correlations of the received signal with the stored version of the specific signature of the tag will result in high signal-to-noise at the receiver and high accuracy of positioning and tracking algorithms. Another method uses polarization analysis to enhance the signal-to-noise ratio. Conventional time-frequency and digital filtering manipulations may be used additionally to the tag-specific detection algorithm to enhance the signal-to-noise even further. The system can also be placed in an anechoic room to avoid abundant multipath reflections.

Embodiments of the invention can be applied in many different communication schemes all involving UWB signals which have an imprint of the resonant tags. The communication scheme may be a simple pulse echo scheme, where a single pulse is transmitted and is scattered, reflected or transmitted by the tag and received. The analysis of the resonant tag signature in the received signal gives accurate distance to a target from time of travel of the pulses. When a sequential series of signals are analyzed, successive positions may be determined and used for motion analysis or position tracking. The scattering properties of the tags can also give accurate information on the orientation of the tag within its environment. Detection of one tag by different receivers can give absolute geopositioning information. Generally three receivers are used when 3-dimensional coordinates are needed and two receivers are used when 2-dimensional coordinates are needed. More receivers may be used and result in an overdetermined system, but can still extract the information using estimation algorithms. Different tags may be used and cross-correlation of different scattered tag signals will give information on relative locations of the different tags. In true multipath mode, one or more different passive or active tags are detected by one or more different transceivers (transmitters or receivers) and spatial correlations between all transceived signals can give absolute and relative positioning information on all tags. Each transceiver may consist of a single or multiple antenna(s). The communication scheme may also involve two or more UWB pulses or impulses separated in time over 1-100 ns, where the first pulse excites the resonance and the second pulse probes the resonance of the tag, similarly to what is generally done in time domain pump probe schemes. In the imaging mode, scattered signals are recorded while scanning the UWB signal by beamforming using antenna's, antenna grid or antenna baselines and advanced beam focusing methods. The image may result from sequential analysis of each scattered signal but also cross-correlation information between different signals may be used to enhance the imaging processing, to enhance the contrast.

Medical monitoring and imaging applications are a good application domain of embodiments of the invention for a number of reasons. Firstly, the high refraction index $\in_r$ in body tissues in the UWB frequency range, ($\in_r$ is typically between 5-100) increases the accuracy of the positioning with a factor equal to $\sqrt{\in_r}$ as compared to air. Instead of sub-centimeter positioning, sub-millimeter positioning is realistic. Secondly, the average power is low in the case of UWB provided that the pulse length is short in comparison with the repetition rate. The maximum average power that can be emitted is typically limited by regulations due to the damage it can cause to the human body. The regulations typically limit the specific absorption rate (SAR-value), which estimates the amount of radio frequency power absorbed in a unit mass of body tissue over time. UWB signal sources with high peak power can compensate for the dielectric losses typically experienced in body tissues, while keeping the average power absorbed in the body tissues low. The signal-to-noise ratio in the receiver is thus higher for a limited SAR-value. This gives UWB a clear advantage over all narrow band radar systems. However, the signal-to-noise ratio in the receiver for a certain signal power is limited by the small dielectric contrast in the tissues to monitor.

The embodiments do not need to rely on the dielectric contrast between tissues as the signal source. Instead the embodiments can exploit the spectroscopic features of magnetic resonant tags, rather than molecules that are already present in the body, to identify the object. Due to the broad spectral content, the UWB pulse can gather data at a wide frequency range and can reveal spectroscopic features not seen in continuous wave probing. These spectroscopic features of tags have not been exploited in existing medical applications of UWB devices.

The simple processional motion of a spin is the basis for the magnetic excitations and resonances in magnetic materials, including ferromagnetic resonance (FMR) in ferromagnetic and ferrimagnetic materials, electron spin resonance (ESR) in paramagnetic materials, antiferromagnetic resonance in antiferromagnetic materials and nuclear magnetic resonance (in materials containing nuclei with unpaired spins). When the macroscopic magnetization (total net spin) is processing around an applied field in unison, there is a uniform mode. Since the magnetization vector is the volume average of the dipole magnetic moment of the sample, it follows that the individual spins undergo the same precession. The precession of the macroscopic magnetization implies that the individual "spins" are each processing with the same frequency and the same phase. A spin wave is similar in that the individual moments throughout a material process with the same frequency, but with different phase around the external field direction. The spin precession frequency is called the Larmor frequency or resonance frequency $\omega_{resonant}$. It is often described by Landau-Lifshitz and Gilbert equations (LLG equations, and valid in the case of strongly coupled spin systems such as ferromagnetic spin systems).

$$\dot{\vec{M}}(t) = -|\gamma|(\vec{M}(t) \times \mu_0 \vec{H}(t)) + \frac{\alpha}{|M_0|}(\vec{M}(t) \times \dot{\vec{M}}(t)) \qquad [2]$$

Where M(t) the net magnetization, H(t) denotes the total internal field, $\gamma$ is the gyromagnetic ratio and $\alpha$ the Gilbert damping or dissipation factor. The first models a magnetization spinning at Larmor frequency $\omega_{resonant}=2\pi.f_{resonant}$, and the resonant frequency will depend both on M(t) and H(t). The second term models dissipation of motion. Dissipation mechanisms include different spin relaxation mechanisms such as dephasing or dissipation towards the lattice implying heat generation. A conventional magnetic resonance spectrometer consists of a microwave cavity in which a fixed-frequency continuous wave RF magnetic field is applied to the sample. A DC bias field of variable amplitude is applied. When the resonance condition is met, resonant power is absorbed by the sample. The absorbed power will typically have a Lorentzian line shape from which the resonant field corresponding to the resonant frequency (by $H_{resonant}=\gamma \omega_{resonant}$) and line width of the resonance $\Delta H=\gamma.\Delta \omega_t$ (as a consequence of the relaxation) can be obtained. Narrow-band ferromagnetic resonance spectroscopy has been used for over 50 years to study both the resonant field and line width of a variety of ferromagnetic species.

The total internal field H(t) contains both the externally applied field, (in the embodiments of this invention the time-dependent field UWB radiation plus possibly, but not necessarily, any additional static or time-varying magnetic fields applied) and internal contributions. The internal contributions are strongly dependent on the magnetic material, material anisotropy, shape, size and geometry and the stress or strain applied on the material. For example: a nanowire and a nanoparticle made from the same material and with the same diameter will have significantly different resonant frequencies due to their different shape. A magnetostrictive material will have a different resonant frequency depending on the strain applied. |M| can be dependent on the temperature, because of thermal fluctuations of the spins contributing to the net magnetization, and on the magnetic fields applied, which can magnetically saturate the material. The maximal value of |M| is equal to Ms, the saturation magnetization of the magnetic material which typically ranges between 10 kA/m (e.g. for weak or diluted ferromagnetic or ferrimagnetic materials) and 1500 kA/m (for strong ferromagnetic materials).

Using the LLG equation, it is possible to predict theoretically the magnetic response of the tag on UWB pulses typically used in radar applications. FIG. 4 shows the magnetic resonant response both in the time domain and in the frequency domain for a typical UWB pulse and for a ferromagnetic (Permalloy) and a ferrite tag. The permeability at magnetic resonance can be calculated from the LLG equation and is best described as a complex tensor $$[\mu] = \begin{bmatrix} \mu' & j\kappa'' & 0 \\ j\kappa'' & \mu' & 0 \\ 0 & 0 & \mu_0 \end{bmatrix}$$

with $$\mu' = \mu_0 \left( 1 + \frac{\mu_0 \gamma |M|(\omega_{resonant} + j\omega\alpha)}{\omega_{resonant}^2 - \omega^2(1+\alpha^2) + 2j\omega\alpha} \right)$$

$$\kappa'' = \mu_0 \cdot \omega \frac{(\omega_{resonant} + j\omega\alpha)}{\omega_{resonant}^2 - \omega^2(1+\alpha^2) + 2j\omega\alpha}$$

Both $\mu'$ and $\kappa''$ show the same magnetic resonant feature as in FIG. 4. Note that a linearly polarized incident magnetic field H will result in elliptically polarized induction field B=[μ]H close to resonance. Note also that the permeability of the material is approaching $\mu_0$ when going away from the resonant peak, this is often a good approximation at GHz frequencies. If the permeability is larger than $\mu_0$ ($\mu_r$>1) off-resonance, the resonant curve may change in amplitude, but the resonant frequency remains the same. The amplitude, phase and polarization of incident radiation will strongly depend on the frequency close to the magnetic resonance. This is demonstrated in an example S-parameter measurement performed on a tag material having a magnetic resonance in FIG. 5.

Some embodiments of the invention make use of a magnetic resonant response of the medium used for the tag in the frequency range of approximately 500 MHz-20 GHz which is the range as the frequency spectrum of typical UWB signals (See FIG. 2). The materials may consist of ferromagnetic materials such as Co, Fe or Ni or rare earth based alloys, paramagnetic or superparamagnetic materials, ferrimagnetic materials or ferrites, which are, in general, oxides of iron combined with one or more of the transition metals such as magnesium, manganese, nickel, lithium, zinc, or barium e.g. $MnFe_2O_4$. The materials may be nanocomposites of dielectric material containing particles of any of the previous materials, or magnetic materials containing dielectric particles e.g. Fe/C, $Co/SiO_2$, $Co/ZrO_2$, $Co_xPt_{1-x}$:C composites. The nanocomposite may be a polymeric material or organic (human) tissue material loaded with magnetic metallic- or non-metallic particles. The particles may have sizes from 1 nm to 1 micrometer. The tag material may also be a ferrite or non-conducting magnetic material coated on a reflecting metallic tag, thereby doubling the transmission path through the magnetic material. The tag material may also constitute of multiple magnetic layers each having the same or a different resonance frequencies. The tag material may constitute of multiple layers of magnetic and non-magnetic layers, where possible coupling and interference effects may play a role and may shift the resonance frequencies. The medium may consist of any of the previous materials or nanocomposites and can have different shape or size, thereby changing the internal field of the medium (through the demagnetizing field) thus influencing the magnetic resonance frequency $\omega_{resonant}$ and the width of the resonance $\Delta\omega$. Additional external fields may be applied to better match the resonance with the UWB frequency range. The application of external fields higher than 0.3 Tesla is however not desirable since it requires expensive and large magnets, which compromises the purpose of using low-cost UWB transceivers in biomedical applications. When using ferromagnetic materials, which have typically higher magnetization (total spin) at low fields, a resonance within the typical UWB frequency range (approximately 500 MHz-20 GHz) can be created at low magnetic (approximately zero to 0.1 T) fields for any geometry.

One embodiment also includes tags with resonant cavities, whereby the resonant cavity is designed to resonate at frequencies which provide a signature that can be detected by the UWB receiver.

FIG. 3 shows the pulse response of a ferromagnetic thin film element of 50 nm thickness on a step pulse (applied using coplanar waveguides) and probed using the interaction of the ferromagnetic material with light for different values of the external field. This optical method has enabled probing of the time domain response of a ferromagnetic tag and reveals a uniform mode with resonance frequency of about 1-3 GHz decaying in about 1-2 nanoseconds. Where ferromagnetic materials have typically higher magnetization (total spin), ferrimagnetic materials have typically lower dissipation.

The UWB pulse will pick up the resonance, and a resonant feature will be present on the return pulse. From the magnetic resonant response and the (surface) wave impedance of the material (See formula 1), it is possible to estimate the characteristic response of the tag on the incident UWB signal. In embodiments of the invention, the tags may consist of conductive or non-conductive material. In the case of non-conductive material, the magnetic resonance and the permeability tensor will result in an amplitude, phase and/or polarization changing the transmission through the materials and magnetic absorption of radiation in the material. In the case of conductive material the penetration of UWB radiation is limited to the skin depth $$\delta = \sqrt{\frac{2}{\omega\mu\sigma}}$$

which is for most conductors of the order 100 nm-1 micrometer (e.g. the skin depth of aluminum at 5 GHz is on the order of 600 nm). When the conductive tag has a smaller characteristic dimension than the skin depth, the whole volume will be able to absorb radiation and part of the incident radiation may be reflected, but may also be transmitted. Note that higher frequencies penetrate less than lower frequencies. Note also that close to the magnetic resonance the complex permeability tensor changes strongly and so will the skin depth (e.g. the skin depth of Permalloy is reduced to 25 nm at magnetic resonance). This can result in both an increased reflection and in a change in polarization upon reflection/transmission of radiation at magnetic resonance. If the conductive tag has a larger characteristic dimension than the skin depth, the tag will mostly reflect the UWB radio signals, and may absorb a small part at the surface. Thick films (0.1-10 mm) of nanocomposites made of ferromagnetic particles (e.g. Carbon loaded with Fe alloy particles) can be used to reduce the eddy current losses while realizing a desirable strong magnetic resonance of ferromagnetic materials and reasonably high skin depths. The tag may also consist of human tissue loaded with ferromagnetic particles. Such ferromagnetic nanocomposites may be a good choice to create a large signature on the UWB signal. The choice of tag (conductive, non-conductive, composite) will define the optimal receiver placement, to detect reflections or transmissions through the sample.

Embodiments make use of this specific signature that will result on the UWB signal upon scattering on the tag. Electromagnetic radiation with a frequency close to the resonant frequency will change its polarization state, amplitude or phase, due to a different interaction of the electric or magnetic field components parallel and perpendicular to the spins. Since the UWB signals contains these resonant frequencies, certain frequencies of the UWB signal will have changed and the UWB pulse as such will get a specific signature. An example of such signature is presented in FIGS. 4A and 6. The receiver will be able to discriminate this signature from the magnetic resonant tag from any other sources of signals, e.g. multipath reflections and clutter. One possible method to discriminate the signature is to correlate the expected signature with the received signal.

Sub-millimeter accuracy in positioning or position changes of the tags can be measured and can be used to monitor health-related parameters such as uterine contractions, heart beating, breathing, motion of parts of the body (e.g. arms, legs, . . . ) in a telemetric way. Relatively simple low-cost UWB transceivers can be used, monitoring no longer requires expensive scanners or large superconducting magnets to induce magnetic fields. Magnetic resonant tags can be attached to the targeted tissue to be monitored (e.g. at the aorta or the uterus entrance). The specific signature imposed by the magnetic resonance will enable easier discrimination of the signals affected by the tags from other multipath reflections. This can further increase the signal-to-noise ratio in the receiver and make it easier to monitor fetal heart rates, uterine contractions, and so on.

The tags may also be part of a wireless sensor system where the magnetization of the tag is altered in a way to represent the sensor information and will result in different resonant signatures, thereby providing an excellent modulation scheme to transfer UWB signals from the sensor. Multiple tags may represent more complex information, thereby forming a magnetic memory whose state can be probed by UWB signals. The memory can contain an identification code or complex information to be stored. Additional hardware (e.g. magnets) may be necessary to write the magnetization information of the tags.

The tags may be applied by medical surgery, by swallowing, by injection or can stick on a specific part of the body for example. Depending on the application they may have different sizes. E.g. in the case of application by medical surgery (e.g. pacemaker or stent), the magnetic tags may have typical sizes of about 0.1-10 mm. The shape will depend on the application, but will also determine the magnetic resonance.

The tags can be functionalized to specifically bind to certain tissue, cells, organelles (e.g. tumor cells) or to label medicine thereby representing accurate positioning and tracking tags that can be probed using wireless technology. The functionalization of magnetic particles to specifically bind to certain biomolecules is a well known procedure to identify biomolecules in an analyte. The magnetic particles used as a label can be ferrimagnetic, ferromagnetic, antiferromagnetic or superparamagnetic for example and in some embodiments have an average particle size of between 1 and 5000 nm and are therefore called "nanoparticles". Also non-spherical particles such as nanowires, ellipsoids or thin film elements with have a characteristic size between 1 and 5000 nm may be used. Tags may also be part of engineered nanoparticles that can also contain designed functional coatings, molecular targets and drugs enabling protocols of simultaneous targeting, therapy and monitoring.

Metamaterials

Embodiments of the invention can also use another class of materials, known as metamaterials. Metamaterials are a new class of ordered nanocomposites that exhibit exceptional properties in interaction with electromagnetic waves. They are mostly composed of metal-dielectric micro or nanostructures. For certain artificial composite structures, the effective permittivity or permeability of the structure can be entirely different from the permittivities of permeabilities of the composing materials. They may be designed to have a resonant magnetic or dielectric response in the frequency range of approximately 500 MHz-20 GHz. In that case, the resonance will be excited upon incident UWB radiation and will result in a specific signature in the scattered wave.

One known example of such metamaterial is a material consisting of one single or more split ring resonator(s) which each consist of two or more concentric rings separated by a gap, both rings having splits which may be oriented at opposite sides. Such split ring resonator may be designed to have a magnetic resonance in the approximately 500 MHz-20 GHz range. Some design rules were proposed in (Aydin et al. New Journal of Physics 7 (2005) 168). They are typically fabricated by depositing a film of metal (e.g. Au, Al, Cu) on a dielectric and patterning the metal into (an array of) split rings, see FIG. 7 C. Such design enhances the electromagnetic field locally and interacts with the field such that a virtual band splitting is created, similar to the Zeeman band gap in ferromagnetic materials, which translates in a resonance in the permeability. The resonant frequency will depend on the number and size of the rings, gaps and splits used. The sizes of the split ring resonators may by $\frac{1}{3}$th to $\frac{1}{30}^{th}$ of the wavelength of the radiation. Since in the body the wavelength is reduced due to the high dielectric constants, the split ring resonators may be designed smaller than in free space. For split ring resonators with typical diameters of 0.01-20 millimeters, the magnetic resonance can be designed in the range of 500 MHz-20 GHz. The resonance causes a dip in the transmission spectra at the resonance frequency with a typical line width of 0.01-1 GHz. Other designs of metamaterials may also result in a magnetic resonance. Other designs include (combinations of) rings, square or rectangle shaped rings, split rings, nanowires, bended wires made out of a conducting material and arranged on a dielectric host material, with typical dimensions of $\frac{1}{3}$th to $\frac{1}{30}^{th}$ of the wavelength of the radiation. The dielectric host material may also be the human tissue itself.

Some of these metamaterials may have a dielectric resonance in the 500 MHz-20 GHz range. One example of such metamaterials are the closed ring resonators, consisting of two or more concentric rings separated by a gap with a dielectric resonance (resonance in the effective permittivity). The resonance causes a dip in the transmission spectra at the resonance frequency. Some of these metamaterials may have a combined dielectric and magnetic resonance in the 500 MHz-20 GHz range.

When UWB signals are transmitted through such material, a specific signature will result on the transmitted pulse. Any phase shift, amplitude change or polarization change of the incident radiation upon transmission or reflection on a resonant material will result in a signature on the time domain waveform which may be recognized in the receiver and can be used to estimate distance, position of the tag and to track the tag in real time. Such materials may therefore be used as a tag in biomedical applications. No additional magnetic fields are necessary to induce the resonance in this case. Multiple ordered resonator structures or tags may be necessary to make the dip or peaks high enough to create a pronounced signature, which may be easily received. Due to their large dimensions they will mostly be applied by surgery e.g. by using catheters or probes.

Modulation of Tags

The tags may also be part of a wireless sensor system where the magnetization of the tag is altered in a way to represent the sensor information and will result in different resonant signatures (phase), thereby providing an excellent modulation scheme to transfer UWB signals from the sensor. In the case of a metamaterial tag, the tag itself may represent a sensor value (e.g. a ring tag used in a stent with diameter corresponding to the aorta diameter) and a changing diameter will change the resonant frequency and can be probed directly by UWB signals. Multiple tags may represent more complex information, thereby forming a magnetic memory which state can be probed by UWB signals. The memory can contain an identification code or complex information to be stored. Additional hardware (e.g. magnets) may be necessary to write the magnetization information of the tags.

The tag can include magnetic resonant material in the form of a sphere, an ellipse or ellipsoid, an elongated wire, a closed circular or square ring, a split ring or unclosed ring, a ring with multiple splits, two or more concentric rings.

The tag can include magnetic resonant material consisting of an ensemble of N of shapes arranged in periodic or random order, e.g. to store specific information in encoded form which can be useful.

Magnetic Resonant Imaging Techniques

Magnetic resonance imaging (MRI) are well-known techniques to produce high quality tomographic images (2D slices or 3D images) inside the human body. MRI is based on the principles of nuclear magnetic resonance (NMR). MRI commonly uses DC magnetic fields of 1-3 T to magnetize the nuclei. Electromagnetic waves in a narrow-band frequency range are selected to identify resonant properties (frequencies, relaxation times) of specific nuclei. For example, protons are commonly used for imaging of human organs due to the high concentration of $H_2O$ in the body with typical resonant frequencies close to 42 MHz at 1 T. Other nucleus Larmor frequencies are in the range 50 KHz-100 MHz and the entire frequency spectrum of interest in those imaging applications is of the order 10 kHz-1 MHz, which is an extremely narrow band, and the hardware is optimized towards generating and receiving this single-frequency e.g. a heterodyne detector matched to the frequency band of the source. In some MRI experiments a complex pulse sequence of narrowband RF waves is used to manipulate the phase of the nuclei as to create a specific type of NMR signal. The pulse should rotate the spins of the nuclei over exactly 90 or 180 degrees and has to be tuned together with the nuclei resonance and can be 1-2000 microseconds.

In order for any tissue to be visible in an MRI image there must be contrast in the emitted signal (amplitude/phase/frequency) of the nuclei in the targeted and the adjacent tissue. This contrast can originate from differences in nuclear spin relaxation time, nucleus concentration or density. A contrast medium is often introduced into the body to enhance the contrast between the tissues by differential uptake. Paramagnetic or superparamagnetic particles are often used as contrast agents that create oscillating fields when they tumble through a water environment, thereby changing the relaxation times ($T_1$ and $T_2$) of the tissues by introducing randomly fluctuating magnetic fields near the nucleus of interest, e.g. some tumor cells have a greater Gd uptake than the surrounding tissues, thereby decreasing $T_1$ and resulting in strong contrast of tumors in MRI scans. Ferromagnetic resonance (FMR) imaging is a technique which is used for imaging ferromagnetic materials. In U.S. Pat. No. 6,924,150, which is incorporated herein in its entirety by reference, a technique for narrow band radio frequency FMR imaging was proposed. Since the human body does not contain such properties by nature, FMR imaging was never considered for biomedicine applications. In a ferromagnetic material, the ferromagnetic resonance (FMR) signal is much stronger than NMR or other resonances due to the very high spin density and strong exchange coupling between the spins. The same exchange coupling also causes suppression of spin-spin relaxation such that the spin-lattice relaxation will dominate the total relaxation time.

The previous imaging examples never used the ultra-wide band signal sources that are used in UWB radar techniques. In embodiments of this invention, rather than relying on narrowband RF waves, there is use of very short pulses, impulses or pulsed RF sources which are broadband (bandwidth>about 500 MHz typically) and can interact with the magnetic resonant tags. In the time domain, the pulses should therefore have a subnanosecond feature such as subnanosecond rise time or pulse length. By scanning the UWB beam in a part of the body, biomedical imaging applications are possible. The scanning requires highly directional antenna's or antenna arrays and/or beamformers. The advantage of such an UWB scanning device is the low-cost hardware involved for imaging applications. Zero or very low magnetic fields can be used and no expensive magnets as in current MRI imaging devices are necessary. The sample under interrogation may be a tag property, e.g. the location of the magnetic tag or the unique identity, or a biospecimen sample that is "labeled" with a magnetic particle, through molecular or biological attachment.

Exposure to RF radiation during an UWB scan is minimal since the amount of energy required for a UWB scan is significantly less than conventional continuous wave imaging or scanning devices due to the short exposure in time. The radio frequency energy applied during an imaging sequence can cause heating of the tissues of the body and it is therefore recommended that exposure to RF energy is limited. The specific absorption rate (SAR) is the limiting measure and limit the signal-to-noise ratio for continuous wave applications. The SAR values refer to the average power that can be tolerated by body tissues e.g. by the skin. Since the absorbed power is depending on both the frequency and the power of the RF field, the SAR value will limit the source power at a certain frequency. That is why the most popular imaging techniques are those that work at lower frequencies (e.g. MRI) where higher field power can be tolerated. The pulsed power used in UWB gives higher signal-to-noise than continuous wave probing for the same limited SAR value. The source can thus compensate for the high signal attenuation experienced in the body in the frequency range of interest, still giving reasonable signal-to-noise ratios at the detector side. The contrast agent used in nuclear imaging techniques may be used as resonant tags in embodiments of this invention, if the resonance can be excited by the UWB radiation.

Local Stimulation using Magnetic Resonant Tags

It is clear that the UWB radiation excites the magnetic resonance of the tags, resulting in both the excitation of a uniform mode or spin waves, that locally alter the electromagnetic field and resonant heat generation due to the dissipation of the magnetic motion. For most materials the resonant heat generation may exceed the inductive heat generation by any other losses e.g. eddy currents. This has been shown by John Moreland, et al., in Rev. of Sci. Instr., Vol 71 p 3088, which is incorporated herein by reference in its entirety, where ferromagnetic resonant spectroscopy was performed in ferromagnetic materials by measuring the absorbed heat using calorimetric measurement methods. UWB pulses impinging on the tags will almost instantaneously heat the tag due to resonant absorption within the UWB frequency range.

The heat will be transferred from the surface of the tag to the immediate surroundings, i.e. the tissue or the biomolecular bonds with which it is in contact. Since the transfer of heat may occur at very short time scales (nanoseconds), the periodic impingement of tags by short UWB pulses can result in instantaneous heating of the tissue or bonds thereby inducing thermally activated processes. This remotely generated, but very localized (both spatially and in time) heating of biological tissue may be used to trigger an event in its immediate environment, e.g. a biochemical reaction. The advantage is that no bulk heating, but only heating near the surface of the tag will occur. A typical application is hyperthermia, where the magnetic particles are heated, in this case by ferromagnetic resonance heating, and transfer their heat to the environment, thereby destroying cells in direct thermal contact with the particles. The hyperthermia can be used as a cancer treatment. Other examples may be locally induced endothermic reactions at the molecular level, e.g. thermally induced DNA (de-) hybridization, thermally induced denaturation or other conformal changes (e.g. proteins), thermal release of medicine upon radiation; local neurostimuli, etc. . . . The resonant magnetic dipolar or electrical fields excited by the UWB pulses may also act as biochemical stimuli. The UWB signals and resonant tags may also be used in therapeutic devices based on these principles, where the therapy (e.g. release of medicine) is induced by wireless ultra wideband signals. The repetition rate of the UWB pulses may be increased above what is generally used in UWB radar communication (e.g. repetition of a 250 ps pulse every 0.5-100 ns) to enhance the efficiency of the therapy.

Different applications of UWB signals and resonant tags may be combined. In a therapy, for example, both the positioning or imaging device may be combined with the stimulation to first see the location of the tag close to a tumor, and than to treat it, e.g. by hyperthermia only when the tags are positioned at the right place. Another combination may be the thermally induced release of medicine after checking the position of the tag at the targeted position.

Embodiments of the invention are based on magnetic resonant tags excited/probed by ultra wide band radar with resonance frequency in the spectral range of the radar signals. Embodiments of tags can be any of the following, or combinations of these:

Tags: Single resonance frequency or in the neighborhood, harmonics of resonant frequency.

Tags: Magnetic materials e.g. made from ferromagnetic materials, ferrites, paramagnetic materials Tags: Micro and nanoparticles made from magnetic materials showing magnetic resonances Tags: Multilayers of these magnetic materials, multilayer of magnetic materials with other materials.

Tags: Metamaterials showing magnetic resonances

Tags: Other materials (e.g. dielectric materials, polymers, human tissue) loaded with magnetic materials or materials.

Tags: Magnetic properties of tag may be tuned such that a unique ID. (e.g. chain of particles width different resonant properties)

Tags: Tags may consist of multiple tags (e.g. multiple layers) each with unique resonance to generate a kind of barcode.

Tags: Micro and nanoparticles functionalized to target biospecimens by e.g. specific bonding or take up (e.g. brain, cells, organs, organelles)

Tags: Micro and nanoparticles functionalized to have a labeling function. (e.g. drugs labeling)

Tags: part of biochemical platform with coatings, target molecules, drugs, other nanoparticles, and so on, Tags can be transducer activated by UWB radar: e.g. UWB radio can activate medicine release, induce stimulus, etc. . . .

Tags: can be implanted, injected, swallowed, etc. . . .

System Examples

Embodiments of hardware used to probe tags can include a number of ultra wide band transmitter(s), receiver(s) and antennas.

At least one receiver/transmitter can be used to do relative positioning on one line (distance)

At least two to do relative positioning in one plane

At least three to do relative position in space

Baselines or arrays of antenna's to do beam steering (positioning)

A receiver can contain a high bandwidth ADC sampling unit, that might also be gated since high sampling performance is only needed when the signal is expected to arrive. The receiver signals can be correlated in the receiver or on personal computer. The system can have visualization (beam scanner) and storing and analysis software for imaging. The system can be placed inside a anechoic room to avoid abundant multipath reflections on walls and subjects not of relevance.

The External Magnetic field at the tag can be a zero magnetic field or low static magnetic fields (<about 0.3 T). There can be a special orientation of EM field (electric field or magnetic field component) generated by antenna with regard to resonant tags (e.g. perpendicular, parallel to magnetization), which may increase the signal. UWB signals can be used to probe the tags: single pulse or train of pulses, impulse RF cycles or short duration (<1 ns).

Embodiments of UWB communication strategies used in combination with tags can be any of the following:

Pulse echo (reflection or transmission based): Time of arrival gives a real-time distance to a target (excellent for motion analysis); analysis of full time response give you the scattering properties of the tags. Crosscorrelation of different reflected tag signals can give you more information on relative locations of different tags or on sequential locations of single tag (tracking).

Geolocation/Positioning: Pulse leading edge (threshold) detection or time correlations of 1 signal generator/tag by 3 receivers (3D coordinates) or 2 receivers (2D coordinates in a plane or 1 receiver (only distance).

Multipath mode: Different passive or active tags and different receivers. Spatial correlations give you information on absolute and relative distances of the tags.

Figure 1B:
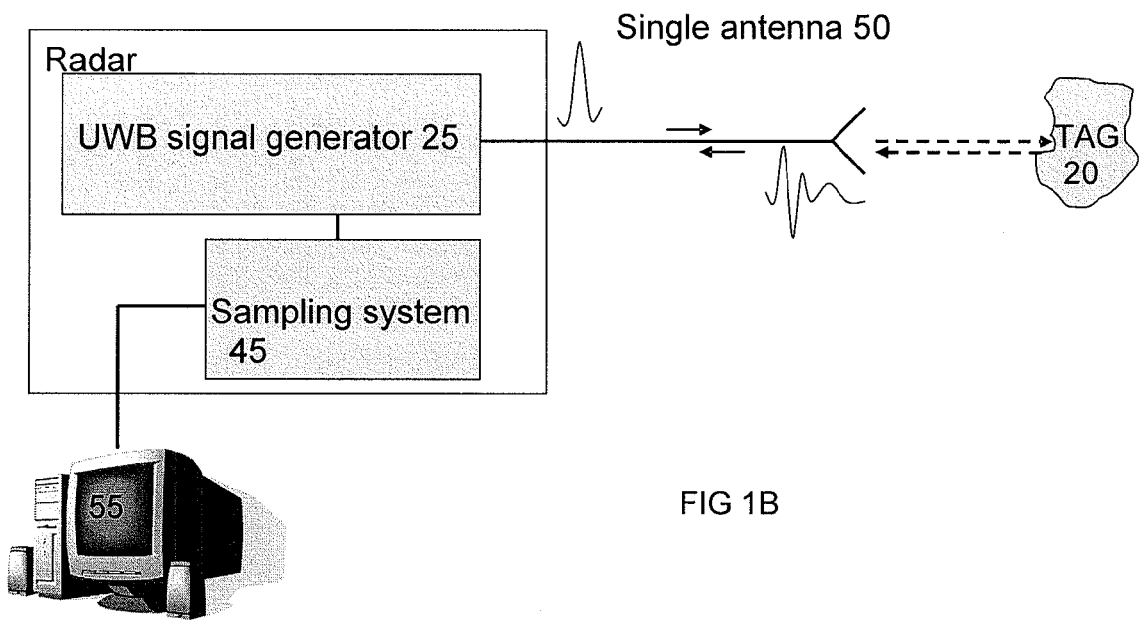
Figure 1C:
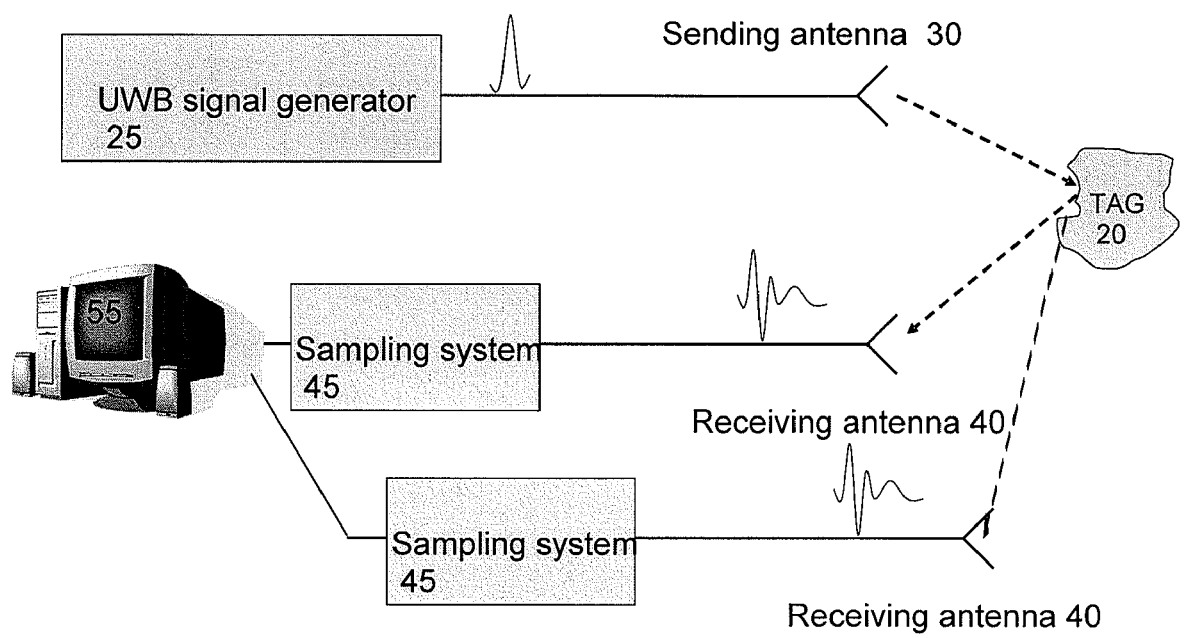
Figure 1E:
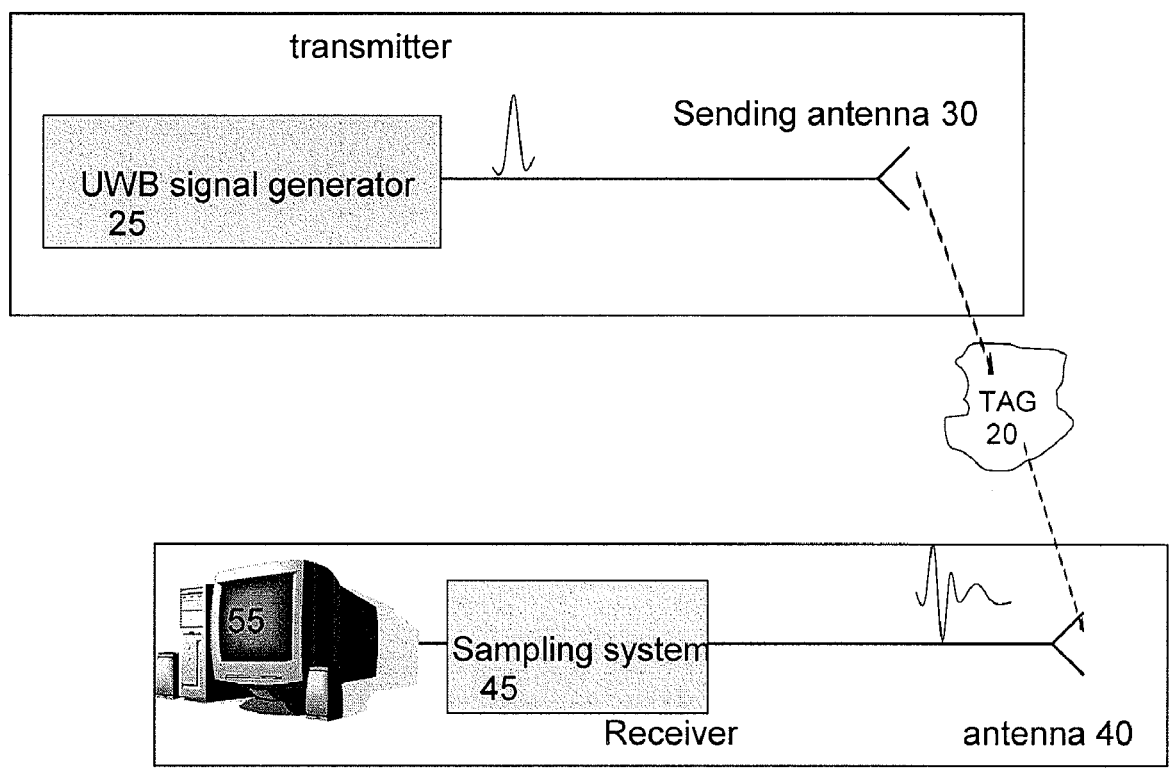

Imaging mode: as before but including scanning or beamforming using antenna grid or antenna baselines FIG. 1A shows an example of a UWB radar system according to an embodiment. Scattered radiation from a tag 20 in a target can be measured using UWB transceivers. The UWB transmitter has a UWB signal generator 25. In this case separate sending 30 and receiving 40 antennas are shown. The receiver typically has a sampling system 45 and further processing capability 55 for discriminating the magnetic resonance response in the form of a signature in the received pulses. Most radars today only use dielectric contrast of target medium with surrounding materials (e.g. heart muscle versus blood). Embodiments of the invention can use magnetic resonant features of the tag. FIG. 1B shows a single antenna 50 used for both transmitting and receiving. FIG. 1C shows an embodiment with a pair of receiving antenna to enable location by time of arrival difference calculations. FIG. 1D shows an embodiment with a pair of transmitting antenna to enable location by time of arrival difference calculations. FIG. 1E shows an embodiment with a receiving antenna 40 located to detect pulses transmitted though the tag. The use of magnetic tags increases the sensitivity of the system of common UWB devices by increasing the signal-to-clutter and signal-to-noise ratio. Therefore it becomes possible to discriminate signals not available for continuous wave radiation with sub mm spatial accuracy. Magnetic tags, as used already in many in vivo applications (e.g. MRI) can now be probed with cheaper radar/telecommunication systems rather than the cumbersome and expensive MRI scanners.

FIG. 2 shows graphs of typical UWB signals in the time domain and frequency domain. For this specific figure the following pulse parameters were used: a Gaussian impulse of 0.5 ns was used to create an RF monocycle (See FIG. 2a) of approximately 1 ns in length. The far field signal after transmission by a dipole antenna is an impulse-like signal, a Gaussian 'doublet' (See FIG. 2b) with two additional zero crossings. A frequency spectrum of this signal (shown in FIG. 2c) has a centre frequency close to 4 GHz and ultra-wide band going from approximately 2-7 GHz.

FIG. 3 shows the experimentally determined time domain response of a ferromagnetic tag when impinged by a step pulse. This response was probed optically by a time-resolved Magneto-optical Kerr microscope. Only one vector component of the magnetization was probed. (Left) Different waveforms represent experimental data taken for different values of an externally applied DC magnetic bias field. (Right) Dependence of the resonant frequency on the internal magnetic field, consisting of the external DC bias field, the internal anisotropy field and the applied step pulse.

Figure 4A:
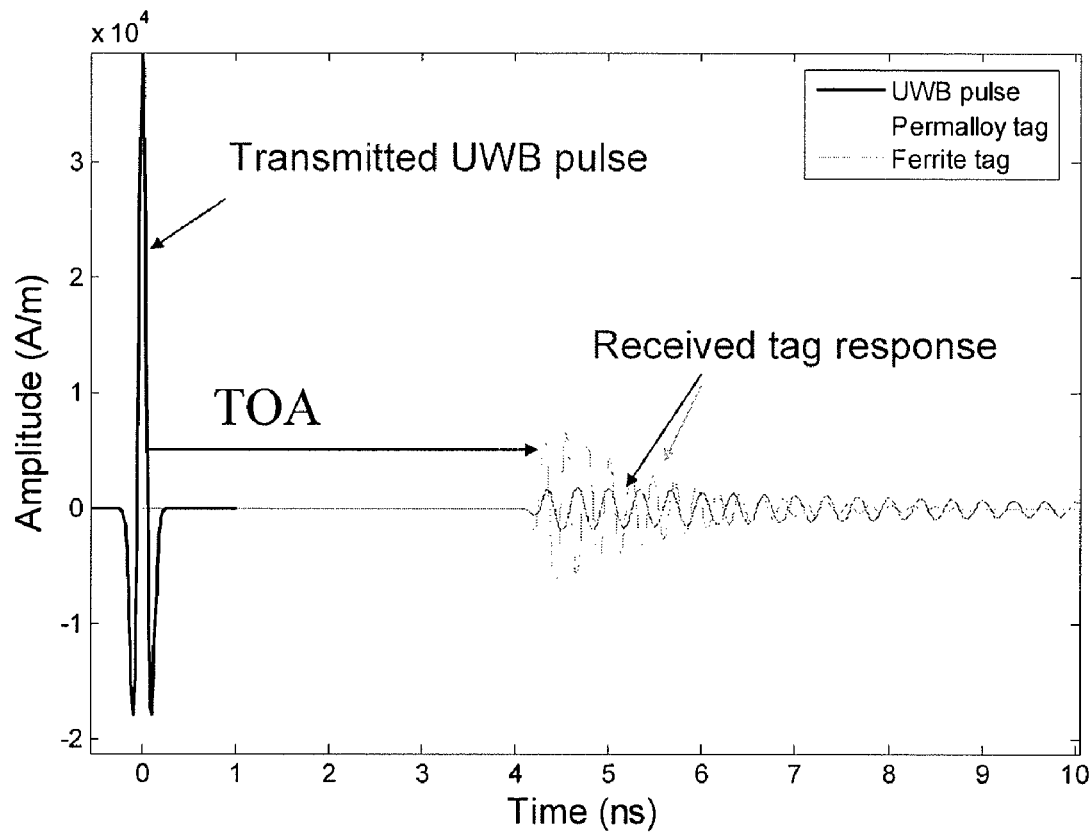
FIG. 4A shows a graph of the simulated response in an ideal antenna of a magnetic resonant tag (made from Permalloy or ferrite) in the time domain, when impinged by a Gaussian doublet, transmitted by the same antenna.
Figure 4B:
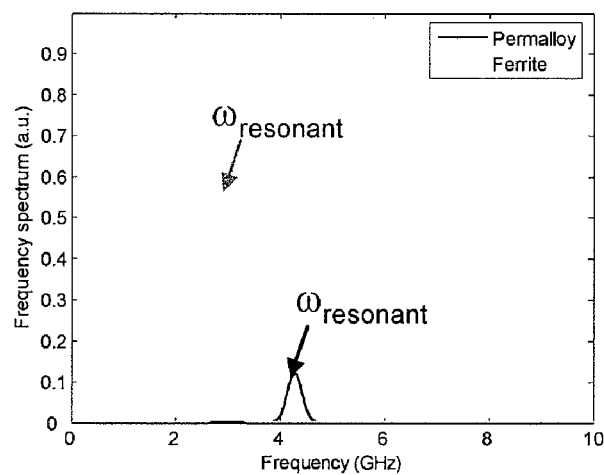
FIG. 4B shows a graph of the simulated tag response in the frequency domain.

FIG. 4 shows the response of the magnetization on incident UWB radiation transmitted from a distance of 60 cm in air (or 20 cm in fat tissue). We have calculated the response both in the time domain (FIG. 4A) and the frequency domain (FIG. 4B) upon an Gaussian doublet impulse with parameters given in FIG. 2b). The Permalloy tag had parameters Ms=840 kA/m and Hk=1 kA/m and α=0.01, the ferrite tag had Ms=240 kA/m and Hk=16 kA/m and a=0.005. No external field was applied. The UWB pulse excites a processional response in both tags. Both tags have magnetic resonances that match the UWB frequency range. The time lag of the resonant response corresponds to twice the distance between the tag and the transmitting/receiving antenna.

Figure 5:
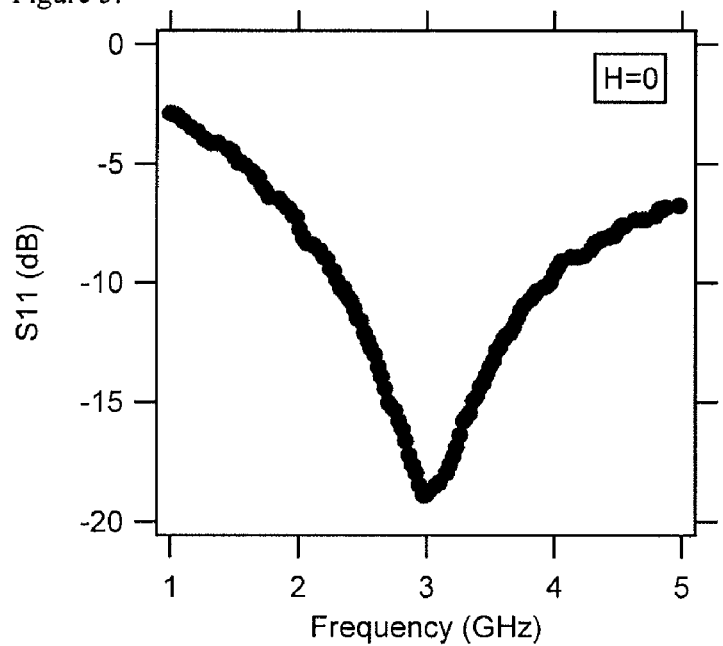
FIG. 5 shows a graph of S-parameters from ferrite tag material showing magnetic resonance at 3 GHz, in zero magnetic field and using narrow-band radiation.

FIG. 5 shows an example measurement of S-parameters from ferrite tag material showing magnetic resonance at 3 GHz. The measurement was performed in zero magnetic field and using narrow-band radiation.

Figure 6:
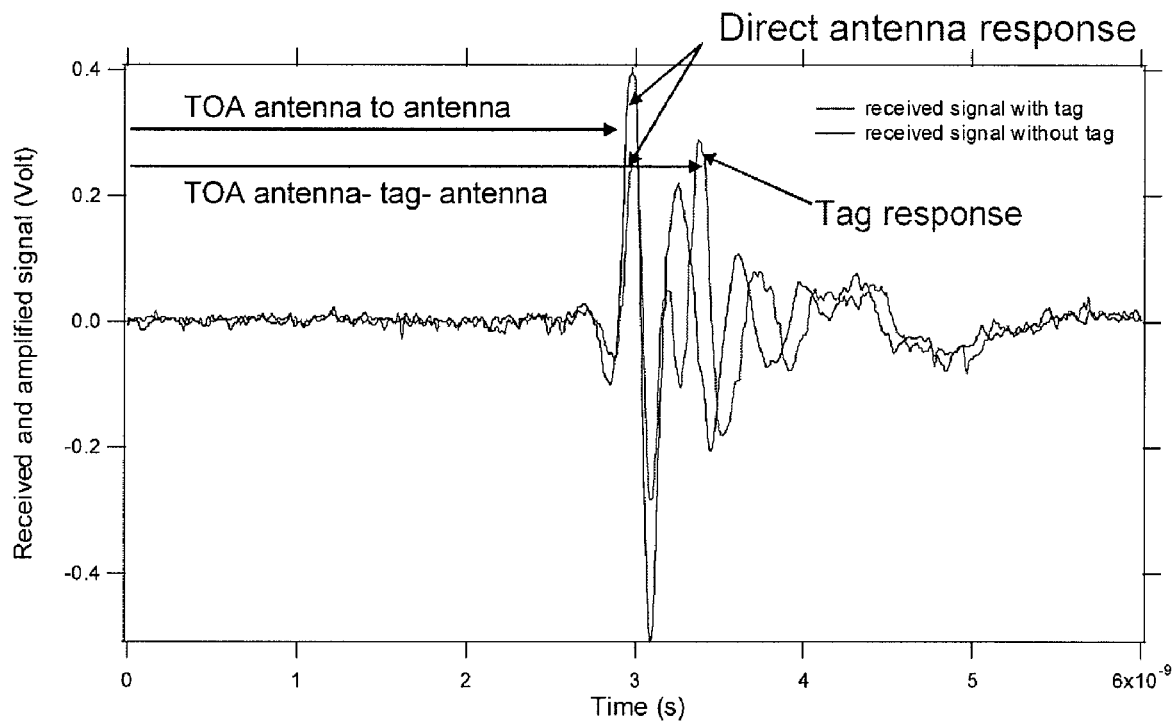
FIG. 6 shows a graph of the first measurement of tags with resonant magnetic response performed by UWB (using non-ideal antenna's with too small bandwidth). The tag response is clearly visible in the echo, superposed on the non-ideal antenna ringings.

FIG. 6 shows an example measurement of the tag response of a metamaterial consisting of an array of 1.5 cm rings in air with magnetic resonance at 3.5 GHz (checked by narrowband methods). The measurement set-up corresponds to FIG. 1A, where a UWB pulse generator with pulse width 250 ps, two dipole antennas (at interdistance 7 cm) and a sampling oscilloscope were used. The tag was positioned in the middle of the propagation path between the antenna's. The dipole antennas were not optimized for this purpose and the direct antenna-to-antenna propagation showed a ringing response. With the resonant tag, the direct antenna-to-antenna propagation is attenuated and a resonant signature of the tags is superposed on the antenna response.

Figure 7:
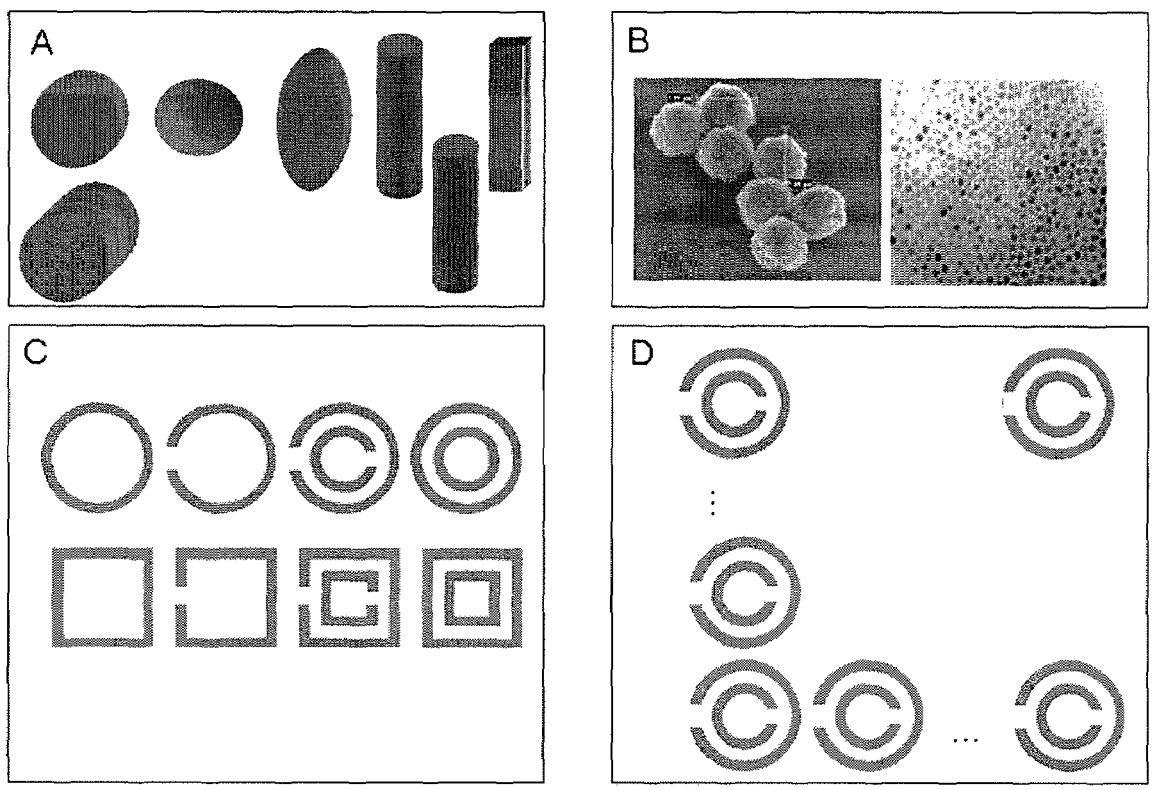
FIG. 7 shows examples of Tag geometries.

FIG. 7 shows different tag geometries that can be used for the purpose of creating magnetic resonances in the UWB range. FIG. 7A shows examples of different shapes of ferromagnetic tags or tags consisting of ferromagnetic materials alternated with other layers. FIG. 7B shows pictures of medium loaded with ferromagnetic tags, the left picture shows particles of 1 micrometer in diameter, the right picture shows particles of 10 nm in diameter. FIG. 7C shows different shapes of metallic shaped particles, that show a magnetic resonance due to their specific designed geometry. Such particles form the atoms of a metamaterial, but can by itself already form a tag. FIG. 7D shows a metamaterial consisting of an array of metal particles.

Applications include biomedicine, health monitoring, imaging, health monitoring devices, algorithms, procedures. Additional applications include e.g. non-destructive testing. For example: wireless monitoring of (magnetically coated) oil tanks in remote places.

Any ferromagnetic resonant properties in the time domain at UWB frequencies can be used. Of particular interest are ferromagnetic nanoparticles for biosensors and health applications.

The embodiments described show some or all of the following features: a detection system comprising a transmitter for transmitting a series of pulses of UWB electromagnetic radiation, at least one receiver for identifying echo pulses of the series of pulses and being adapted to identify a signature imposed on the echo pulses, the signature being indicative of material exhibiting magnetic resonance induced by the series of pulses.

Optionally the transmitted pulses of UWB electromagnetic radiation have a fractional bandwidth of at least 20% and center frequencies between 500 MHz and 20 GHz. Optionally the receiver contains a correlator circuit to identify the signature of the material. Optionally the receiver is arranged to identify the signature by determining any one or more of: a change in pulse shape, a time lag, polarization changes, and a frequency spectrum of the pulse.

Optionally the magnetic resonant material is selected from any of: a ferrimagnetic material, a ferromagnetic material, antiferromagnetic material, superparamagnetic material and a metamaterial showing magnetic resonance within the fractional bandwidth of the transmitted pulse. Optionally the material is shaped as shown. Optionally the receiver is arranged to determine the distance of the magnetic resonant material to the receiver by determining a Time-Of-Arrival. The detection system can have at least two receivers adapted to determine a location of the magnetic resonant material by Time of Arrival and/or Angle of arrival.

The detection system can be arranged to determine the relative location of two magnetic resonant materials by determining a time difference of arrival. The magnetic resonant material can be part of an electronic identification tag. The material can be located in a magnetic field of <about 0.3T. The transmitted pulses of UWB electromagnetic radiation can have a fractional bandwidth of about 20% to 200%, preferably the bandwidth should be larger than the fractional bandwidth of the resonant tag, which can be 1-20% up to 25% or up to 200%. Another aspect is a receiver for receiving echoes of a series of pulses of UWB electromagnetic radiation, and comprising:

a discriminator or correlator circuit for identifying echo pulses from the series of pulses and being adapted to identify a signature imposed on the echo pulses, the signature being indicative of reflection from a material exhibiting magnetic resonance induced by the series of pulses.

Another aspect is a receiver for detecting a material having a magnetic resonance response to illumination by pulses of UWB electromagnetic radiation, the receiver having: a detector for detecting the pulses after they have interacted with the material, and a discriminator arranged to identify in the detected pulses the magnetic resonance response of the material. Optionally the receiver has a signal processor arranged to determine any one or more of: a distance from the material by determining a time of travel of the detected pulses, successive positions of the material, for motion analysis or position tracking, an orientation of the material.

Optionally the receiver has multiple receive antennas and is arranged to carry out a spatial correlation to determine positioning in two or three dimensions.

The discriminator can be arranged to discriminate between different magnetic resonance responses from an active material, or from multiple materials having different responses. The receiver can have a processor arranged to generate an image from scanning of the pulses or scanning of a receiver across the material. A system can have a transmitter and the receiver set out above. The system can have multiple antennas for illuminating the material from different angles, the receiver being arranged to distinguish the pulses from the different angles. The system can be arranged to transmit a beam and scan the beam across the material, the receiver being arranged to determine a location of the material according to the scanning of the beam.

The system can be arranged to send separate pulses to excite a resonance and to probe the excited resonance, the receiver being arranged to distinguish between the exciting and the probe pulses. The system can be arranged for scanning internal parts of a human or animal body.

Another aspect provides a method of scanning an item tagged with a tag having a material having a magnetic resonant response, the method having the steps of illuminating the item with pulses of UWB electromagnetic radiation, detecting the pulses after they have interacted with the material, and identifying in the detected pulses the magnetic resonance response of the material. Optionally the tag is an active tag, and the method has the step of using the pulses to activate the tag.

Optionally the item is a human or other animal body.

Another aspect provides a method of activating a tag in an item, the tag having a material having a magnetic resonant response, the method having the step of illuminating the item with pulses of UWB electromagnetic radiation, such that the magnetic resonance response of the tag causes activation of the tag. The activation can be localized heating or sufficient magnetic resonance to be detected by other means for example. Another aspect provides a tag for use by the system, receiver or method of any preceding claim, the tag having a material having a magnetic resonance response arranged to provide an identifiable magnetic resonance signature response to illumination by pulses of UWB radiation, such that different tags can be identified and distinguished by their signatures.

Other variations can be envisaged within the scope of the claims.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A detection system comprising:
   a transmitter configured to transmit a series of pulses of ultra-wideband (UWB) electromagnetic radiation; and
   at least one receiver configured to receive echo pulses of the series of UWB pulses and to identify a signature in the echo pulses, the signature being indicative of a material exhibiting magnetic resonance induced by the series of pulses.

2. The detection system according to claim 1, wherein the transmitted pulses of UWB electromagnetic radiation have a fractional bandwidth of at least 20% and center frequencies between about 500 MHz and 20 GHz.

3. The detection system according to claim 1, wherein the receiver comprises a correlator circuit to identify the signature.

4. The detection system according to claim 1, wherein the receiver is configured to identify the signature by determining at least one of the following: a change in pulse shape, a time lag, polarization changes, and a frequency spectrum of the pulse.

5. The detection system according to claim 1, wherein the magnetic resonant material is one of the following: a ferrimagnetic material, a ferromagnetic material, an antiferromagnetic material, a superparamagnetic material, and a metamaterial showing magnetic resonance within the fractional bandwidth of the transmitted pulses.

6. The detection system according to claim 5, wherein a shape of the magnetic resonant material is one of: a sphere, an ellipse or ellipsoid, an elongated wire, a closed circular or square ring, a split ring or unclosed ring, a ring with multiple splits, two or more concentric rings.

7. The detections system according to claim 6, wherein a shape of the magnetic resonant material comprises an ensemble of N shapes arranged in periodic or random order.

8. The detection system according to claim 1, wherein the receiver is configured to determine the distance of the magnetic resonant material to the receiver by determining a time-of-arrival.

9. The detection system according to claim 1, wherein the system comprises at least two receivers and the receivers being configured to determine a location of the magnetic resonant material by time-of-arrival and/or angle of arrival.

10. The detection system according to claim 1, wherein the system is configured to determine the relative location of two magnetic resonant materials by determining a time difference of arrival.

11. The detection system according to claim 1, wherein the magnetic resonant material is a part of an electronic identification tag.

12. The detection system according to claim 1, wherein the magnetic resonant material is located in a magnetic field of approximately <0.3T.

13. The detection system according to claim 1, wherein the transmitted pulses of UWB electromagnetic radiation have a fractional bandwidth of approximately 20% to 200%.

14. A receiver for receiving echoes of a series of pulses of ultra-wideband (UWB) electromagnetic radiation, the receiver comprising:

a detection unit configured to identify a signature in echo pulses of a series of pulses of ultra-wideband electromagnetic radiation, the signature being indicative of reflection from a material exhibiting magnetic resonance induced by the series of pulses.

15. A receiver according to claim 14, wherein the detection unit comprises a correlator circuit for identifying echo pulses from the series of pulses.

16. A receiver for detecting a material having a magnetic resonance response to illumination by pulses of ultra-wideband (UWB) electromagnetic radiation, the receiver comprising:
   a detector configured to detect the pulses after they have interacted with the material; and
   a discriminator configured to identify in the detected pulses the magnetic resonance response of the material.

17. The receiver according to claim 16, further comprising a signal processor configured to determine one or more of the following: a distance from the material by determining a time of travel of the detected pulses, successive positions of the material for motion analysis or position tracking, and an orientation of the material.

18. The receiver according to claim 16, further comprising a plurality of receive antennas configured to carry out a spatial correlation to determine positioning in two or three dimensions.

19. The receiver according to claim 16, wherein the discriminator is configured to discriminate between different magnetic resonance responses from an active material, or from multiple materials having different responses.

20. The receiver according to claim 16, further comprising a processor configured to generate an image from scanning of the pulses or scanning of a receiver across the material.

21. A system comprising:
   a transmitter of pulses of ultra-wideband (UWB) electromagnetic radiation; and
   a receiver configured to detect a material having a magnetic resonance response to illumination by pulses of UWB electromagnetic radiation, the receiver comprising:
      a detector configured to detect the pulses after they have interacted with the material,
      a discriminator configured to identify in the detected pulses the magnetic resonance response of the material, and
      a processor configured to generate an image from scanning of the pulses or scanning of a receiver across the material.

22. The system according to claim 21, further comprising multiple antennas configured to illuminate the material from different angles, the receiver being arranged to distinguish the pulses from the different angles.

23. The system according to claim 22, wherein the system is configured to transmit a beam and scan the beam across the material, the receiver being arranged to determine a location of the material based at least in part on the scanning of the beam.

24. The system according to claim 22, wherein the system is configured to send separate pulses to excite a resonance and to probe the excited resonance, the receiver being arranged to distinguish between the exciting and the probe pulses.

25. The system according to claim 22, wherein the system is configured to scan internal parts of a human or animal body.

26. A method of scanning an item tagged with a tag having a material having a magnetic resonant response, the method comprising:
   illuminating the item with pulses of ultra-wideband (UWB) electromagnetic radiation;
   detecting the pulses after they have interacted with the material; and
   identifying in the detected pulses the magnetic resonance response of the material.

27. The method according to claim 26, wherein the tag is an active tag, and the method further comprises using the pulses to activate the tag.

28. The method according to claim 26, wherein the item is a human or other animal body.

29. A method of activating a tag in an item, the tag having a material having a magnetic resonant response, the method comprising:
   illuminating the item with pulses of ultra-wideband (UWB) electromagnetic radiation such that the magnetic resonance response of the tag causes activation of the tag.

30. The method according to claim 29, wherein the tag is activated thermally by magnetic resonance heating of the tag caused by the illumination of the tag by UWB electromagnetic radiation.

31. A resonant tag for being read with ultra-wideband (UWB) radiation comprising:
   a material having a magnetic resonance response configured to provide an identifiable magnetic resonance signature response to illumination by pulses of UWB radiation, such that different tags can be identified and distinguished by their signatures.

32. A resonant tag for being read with ultra-wideband (UWB) radiation comprising:
   a material having a magnetic resonance response configured to provide a resonance frequency related to at least one parameter that represents a sensor value being probed by pulses of UWB radiation, such that it acts as a wireless sensor.

* * * * *